(12) United States Patent
Silvestri et al.

(10) Patent No.: US 7,113,827 B2
(45) Date of Patent: Sep. 26, 2006

(54) DETERMINING THE PRESENCE AND TYPE OF PROBE ASSOCIATED WITH AN ACTIVE IMPLANTABLE MEDICAL DEVICE, IN PARTICULAR A CARDIAC PACEMAKER

(75) Inventors: Luigi Silvestri, Albiano D'Ivrea (IT); Stefano Franceschini, Strambino (IT)

(73) Assignee: ELA Medical S.A.S., Montrouge (FR)

( * ) Notice: Subject to any disclaimer, the term of this patent is extended or adjusted under 35 U.S.C. 154(b) by 92 days.

(21) Appl. No.: 10/759,870

(22) Filed: Jan. 16, 2004

(65) Prior Publication Data
US 2004/0220625 A1    Nov. 4, 2004

(30) Foreign Application Priority Data
Jan. 17, 2003   (FR) .................................. 03 00465

(51) Int. Cl.
*A61N 1/18* (2006.01)
*A61N 1/37* (2006.01)

(52) U.S. Cl. ................ 607/28; 607/27; 607/9
(58) Field of Classification Search ................ 607/28, 607/27, 2, 4, 11, 18
See application file for complete search history.

(56) References Cited

U.S. PATENT DOCUMENTS

| | | | |
|---|---|---|---|
| 4,532,931 A * | 8/1985 | Mills | 607/9 |
| 4,964,407 A * | 10/1990 | Baker et al. | 607/27 |
| 5,431,692 A * | 7/1995 | Hansen et al. | 607/28 |
| 5,476,485 A * | 12/1995 | Weinberg et al. | 607/28 |
| 5,534,018 A * | 7/1996 | Wahlstrand et al. | 607/27 |
| 5,571,156 A * | 11/1996 | Schmukler | 607/116 |
| 5,741,311 A * | 4/1998 | Mc Venes et al. | 607/28 |
| 6,016,447 A * | 1/2000 | Juran et al. | 607/27 |
| 6,317,633 B1 * | 11/2001 | Jorgenson et al. | 607/28 |

FOREIGN PATENT DOCUMENTS

WO    WO 02/18009 A1    3/2002

* cited by examiner

*Primary Examiner*—Robert E. Pezzuto
*Assistant Examiner*—Brian T. Gedeon
(74) *Attorney, Agent, or Firm*—Orrick Herrington & Sutcliffe, LLP

(57) ABSTRACT

Determining the presence and type of a probe associated with an active implantatable medical device, in particular a cardiac pacemaker and devices having similar pacemaker functionality. This device includes circuits for producing monopolar or bipolar stimulation pulses, selectively with or without disconnection of a connection (S1, S2) to a reference potential, and a circuit for sensing a pulse signal produced by the variation of potential induced on one and/or the other of terminals (RING, TIP) and/or on the metallic case (CASE) in response to an application of stimulation pulses. The device operates to analyze a characteristic of the shape (28), in particular the pulse width, and to deliver an indicator representative of the presence or the absence of a probe. The device also can selectively modify at least one operating parameter of the device according to the delivered indicator.

21 Claims, 6 Drawing Sheets

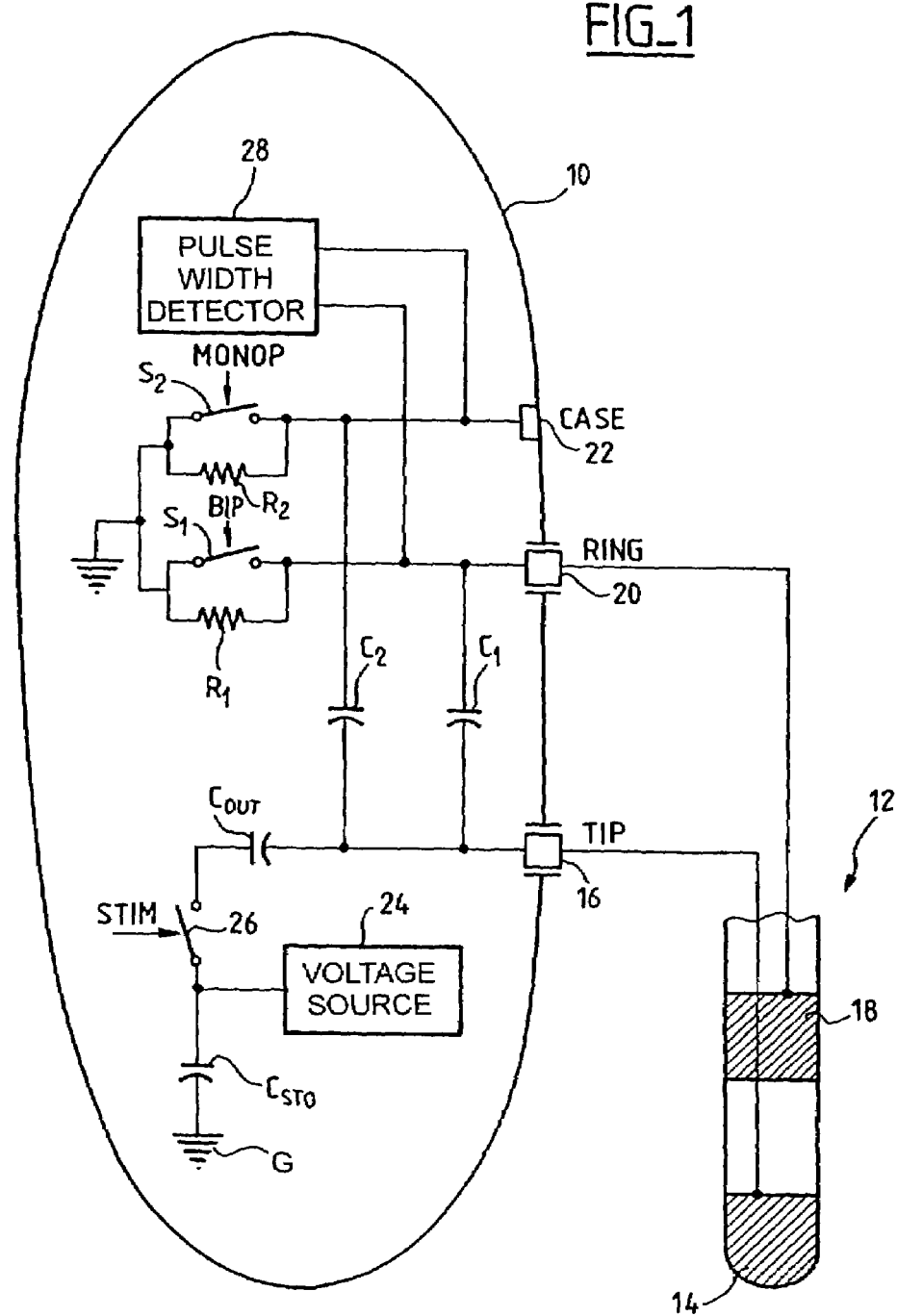
FIG_1

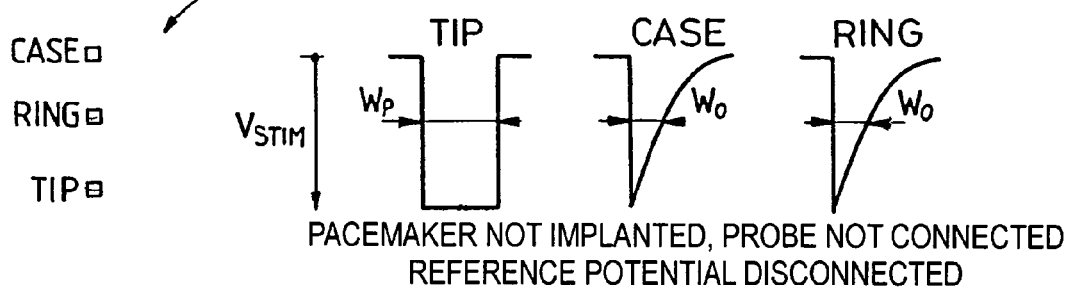
FIG_2 PACEMAKER NOT IMPLANTED, PROBE NOT CONNECTED REFERENCE POTENTIAL DISCONNECTED
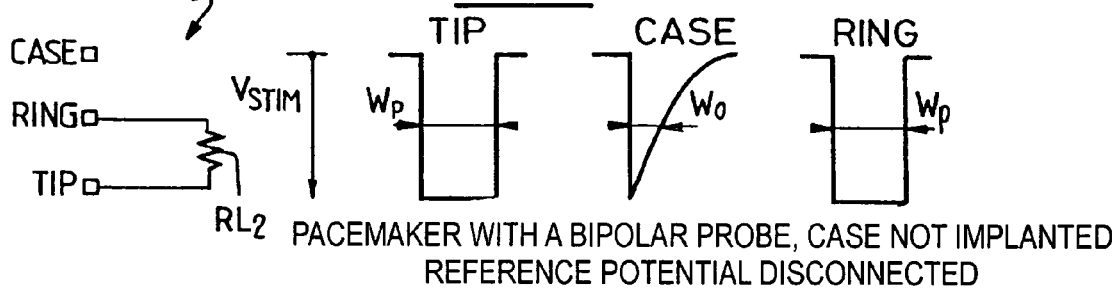
FIG_3 PACEMAKER WITH A BIPOLAR PROBE, CASE NOT IMPLANTED REFERENCE POTENTIAL DISCONNECTED
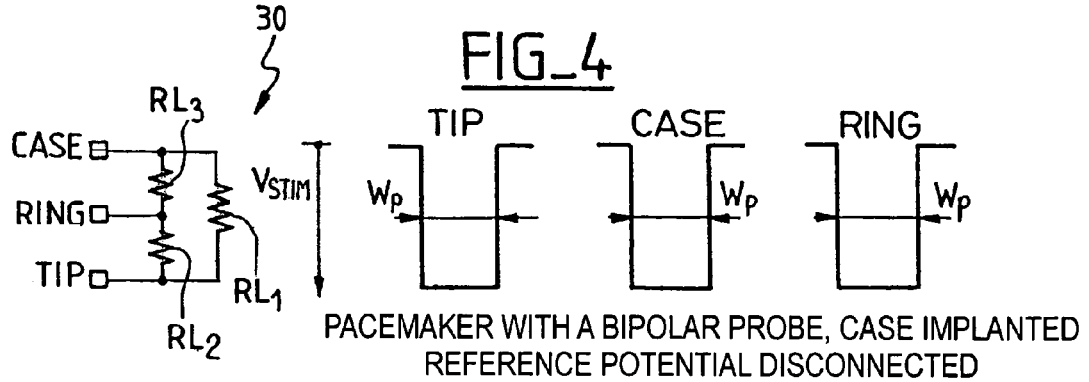
FIG_4 PACEMAKER WITH A BIPOLAR PROBE, CASE IMPLANTED REFERENCE POTENTIAL DISCONNECTED
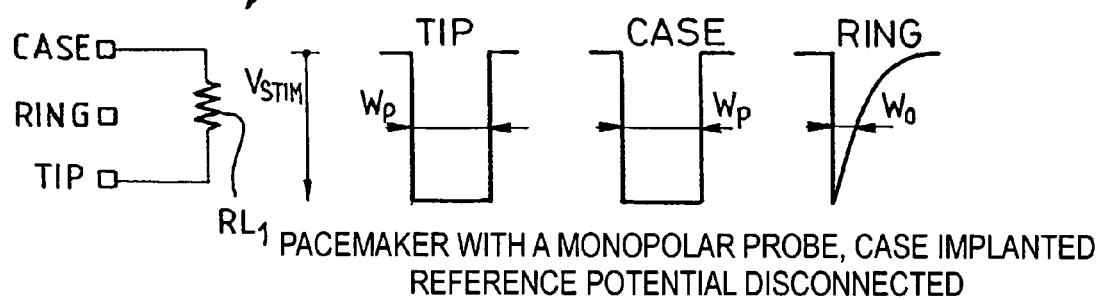
FIG_5 PACEMAKER WITH A MONOPOLAR PROBE, CASE IMPLANTED REFERENCE POTENTIAL DISCONNECTED

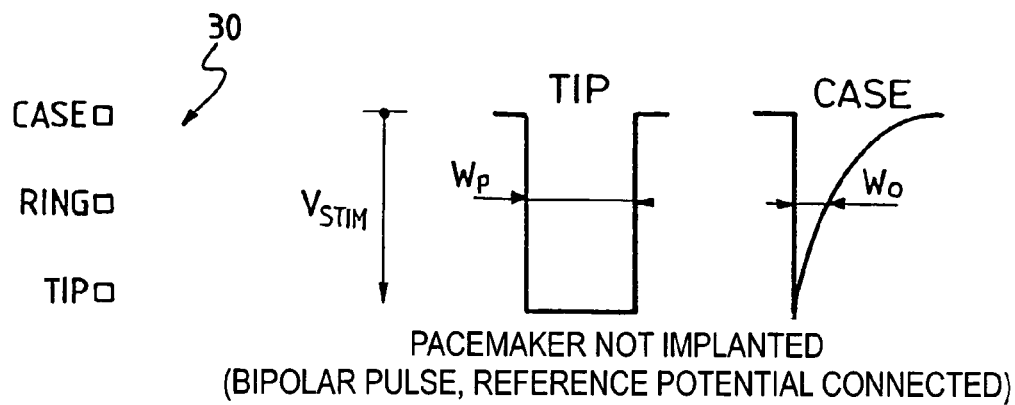
FIG_6
PACEMAKER NOT IMPLANTED
(BIPOLAR PULSE, REFERENCE POTENTIAL CONNECTED)
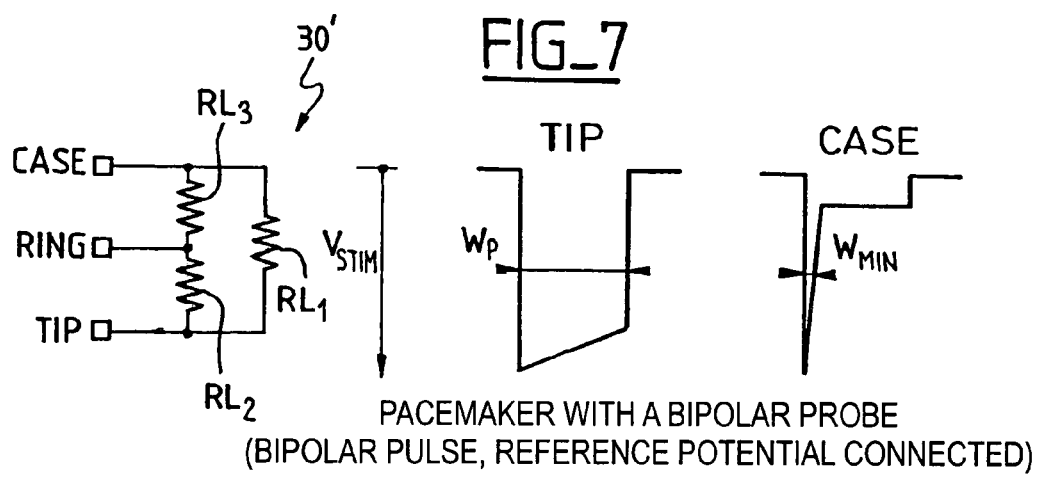
FIG_7
PACEMAKER WITH A BIPOLAR PROBE
(BIPOLAR PULSE, REFERENCE POTENTIAL CONNECTED)
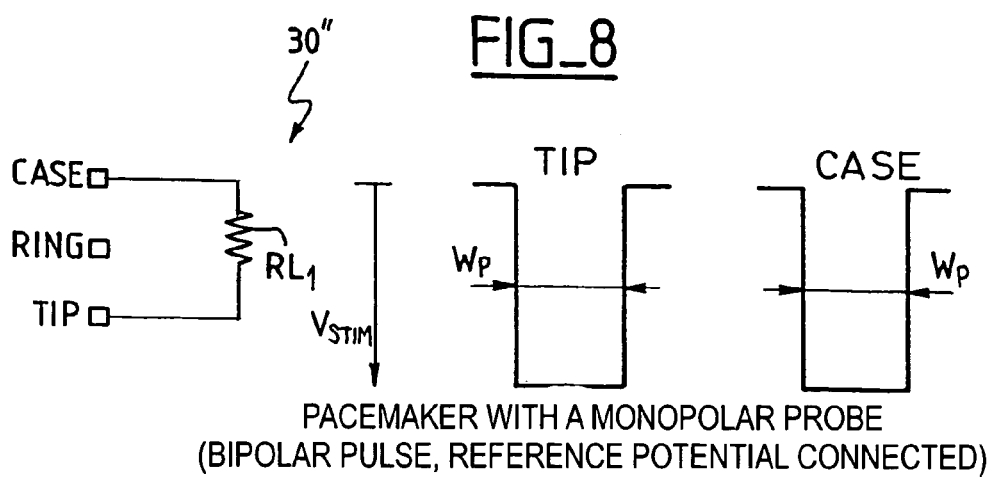
FIG_8
PACEMAKER WITH A MONOPOLAR PROBE
(BIPOLAR PULSE, REFERENCE POTENTIAL CONNECTED)

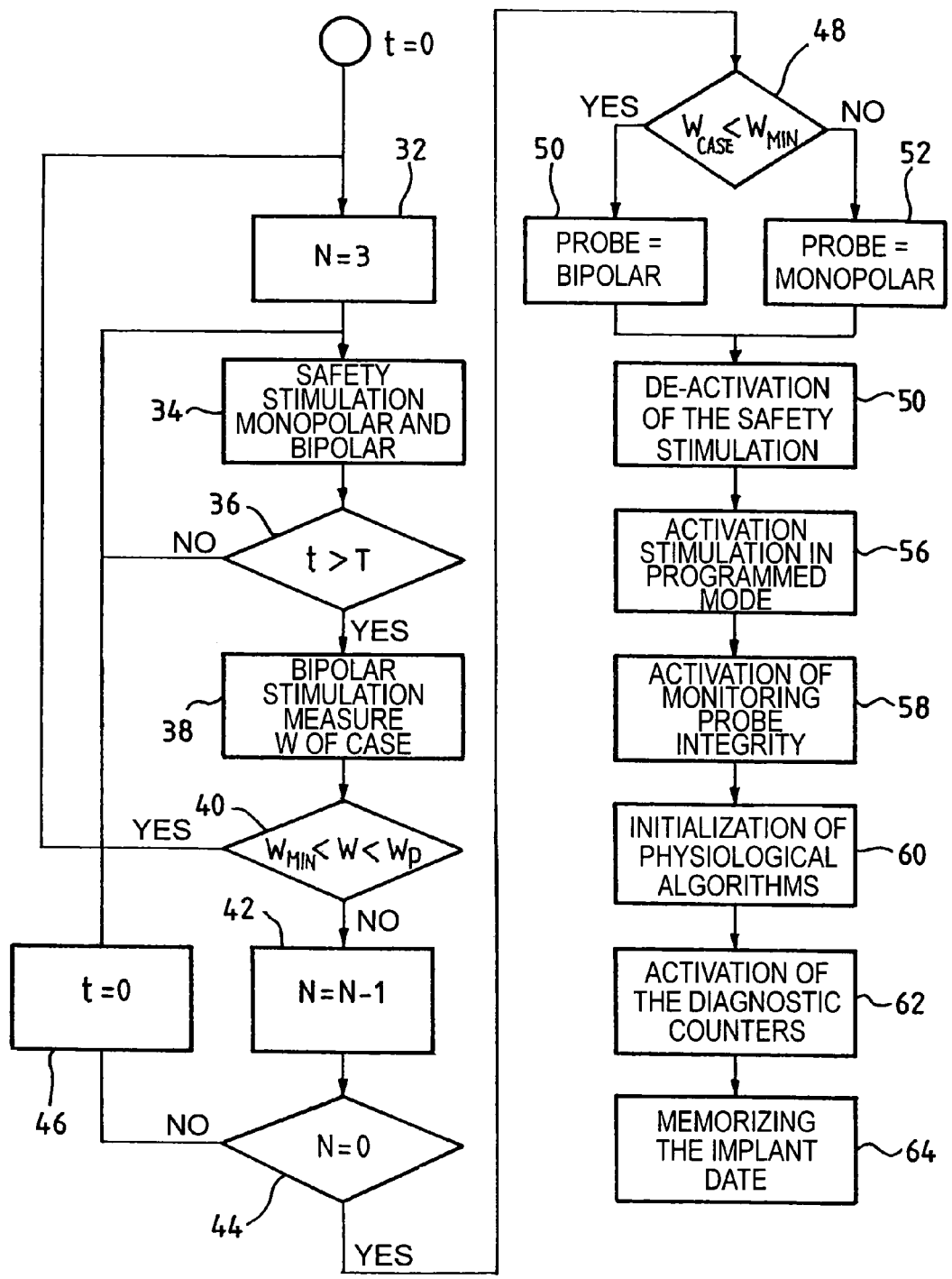

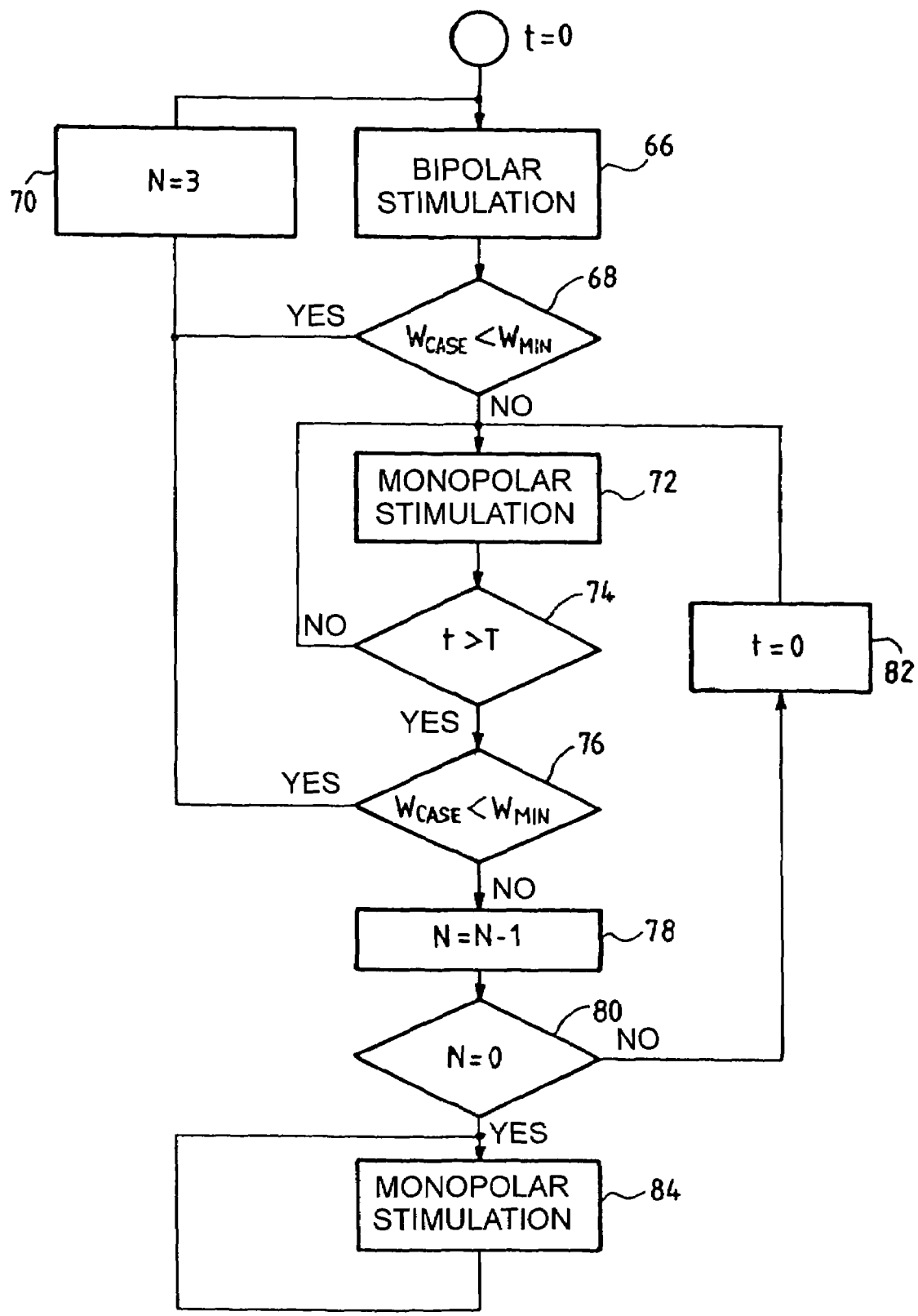
FIG_10

DETERMINING THE PRESENCE AND TYPE OF PROBE ASSOCIATED WITH AN ACTIVE IMPLANTABLE MEDICAL DEVICE, IN PARTICULAR A CARDIAC PACEMAKER

FIELD OF THE INVENTION

The present invention relates to "Active Implantable Medical Devices" as defined by the Jun. 20, 1990 Directive 90/385/CEE of the Council of the European Communities, more particularly to devices such as cardiac pacemakers, defibrillators, cardiovertors and/or "multisite" devices (for sensing and stimulation in multiple (3 or more) cardiac chambers) able to deliver to the heart pulses of low energy for the treatment of the disorders of the cardiac rhythm.

BACKGROUND OF THE INVENTION

Active implantable medical devices typically include a generator having a metallic case that contains the various electronic circuits and an energy source (battery). At the time of the implantation, the generator is connected electrically and mechanically to an external probe that is equipped with electrodes for intra-cardiac stimulation, making it possible to detect the potentials of depolarization of the myocardium, and to deliver to the myocardium the stimulation pulses produced by the generator.

Generally, it is possible to connect a given generator to one of two different types of probes, monopolar and bipolar. This is done at the choice of the surgeon and according to the type of pathology to be treated. In the case of a monopolar (also called "unipolar") probe, the detection and stimulation are operated between the single electrode and the metallic case of the generator. In the case of a bipolar probe, the detection and stimulation can be carried out either in a differential mode between two electrodes of the probe, or in a common mode between the case of the generator and one or the other of the electrodes. Of course, a general set of internal operating parameters of the generator must be selected according to whether the probe used is monopolar or bipolar: the commutation (switching) of the terminals internal to the generator that are to be used, the collection (detection or sensing) of the depolarization signal, the adjustment of the stimulation parameters, the modification of the control algorithms operating the microprocessor, etc.

It will be understood that any error in the selection of the type of operation (monopolar or bipolar) can involve extremely serious consequences. For example, if the device is programmed for a bipolar stimulation but is equipped with a monopolar probe, this error will cause a loss of sensing and the application of an inappropriate stimulation, with a significant risk for the patient. In addition, after the manufacture of the generator, there can be a significant lapse of time between the shipping of the generator and its implantation in the body of the patient. This time can even reach one year to eighteen months. During this sometimes lengthy storage period preceding the implantation, it is essential that the apparatus, whose battery was connected right before shipping, presents an energy consumption that is as reduced as possible, so that the storage period does not have a notable incidence on the useful lifespan of the apparatus, i.e., the duration during which it will be functional after implantation.

With this objective, the device, and in particular its microprocessor, are placed in a sleeping mode having a very low energy consumption. Moreover, it is envisaged to have a mechanism interior to the device to detect the connection of a probe. In this way, the device can detect an implantation and awaken the circuit of the generator, to make it fully functional and to initialize a certain number of parameters, to memorize the starting data, etc. This function of activation can be fulfilled in various ways. For one example U.S. Pat. No. 5,350,401 envisages an activation pin having to be withdrawn by the surgeon from the pacemaker at the time of the implantation, to authorize a communication connection with an external programmer that will send a deactivation control signal to the pacemaker to deactivate the inhibition and allow normal operation.

U.S. Pat. Nos. 5,522,856 and 5,370,666 detect the insertion of a probe by an impedance measurement that is carried out between the terminals of the connector head of the device. In the absence of a probe, the impedance is extremely high. As a probe is inserted, the impedance value decreases below a certain threshold. Crossing that threshold is detected to switch the pacemaker from the sleeping state mode to a mode where it becomes completely awake and functional.

OBJECTS AND SUMMARY OF THE INVENTION

It is, therefore, an object of the present invention to propose a circuit that can, in an entirely automatic way, detect the connection of a probe in order to switch the device from a sleeping state mode at very low energy consumption to an awake mode where all the functionalities will be activated (with, correlatively, a higher level of energy consumption).

As it will be seen, the present invention makes it possible to achieve this goal without any intervention of the surgeon, therefore avoiding any handling or risk of omission (as in the case of a system requiring the insertion of a pin of activation), without continuously carrying out a direct impedance measurement between the terminals, and without recourse to an external programmer.

One aspect of the invention is directed to a device that can, in an entirely autonomous way, not only detect the connection of a probe, but also and especially determine the type of probe used—e.g., monopolar or bipolar—and consequently to commutate and parameterize the various circuits and algorithms of the device appropriately for the type of probe. This function, managed in an entirely automatic way by the device, makes it possible to minimize any risk of error resulting from a lack of conformity between the type of probe used and the programmed operating mode of the device. One thus avoids, for example, any risk of bipolar stimulation applied by error to a monopolar probe.

Another aspect of the invention concerns a device incorporating a safety function allowing for the detection of the particular configuration of the pacemaker, after having been equipped with a bipolar probe, yet before it is introduced into the implantation site (the incision or "pocket" in which the surgeon envisages to place the pulse generator), and when not connected to a reference potential electrode or plate. In this regard, the pacemaker is generally programmed by default in monopolar stimulation mode (e.g., factory set adjustment). In this case, it is important that the generator does not actually deliver monopolar stimulation pulses on the bipolar probe. This is because such pulses would be dangerous because of the absence of return to ground, the case of the generator being electrically in the air (floating potential) during this step. Thus, this safety must be maintained until the final and complete functional activation of the device. It will be seen that the device according to the present invention makes it possible to automatically detect this configuration, and thereby to inhibit the delivery of a bipolar stimulation. However, this inhibition will be maintained only as long as the situation (floating potential) persists, and automatically removed as soon as the connection with the reference potential is restored either by the insertion of the case of the generator in the pocket, or by a connection to a reference potential plate, thus making it possible to electrically close the circuit (to the ground).

The activation of the functionalities of the pacemaker will be thus completely automatic in the case of a bipolar probe. The surgeon will not have to use a reference plate or to force a mode of bipolar stimulation before the generator is installed in the pocket. It will be enough for the surgeon simply to insert the bipolar probe, and the safety will be automatically ensured for the length of time necessary to complete the implantation.

Another aspect of the invention is to propose a device making it possible to ensure a continuous monitoring, cycle to cycle, of the integrity of the probe during the course of operation. This is done in particular to detect a rupture or discontinuity of the wire to the proximal electrode in a bipolar probe, so as to immediately switch the operating mode of the device to a monopolar mode, a mode in which the probe can still remain functional given the rupture.

For this purpose, the invention broadly proposes an active implantable medical device including a metallic case containing a generator, the generator including a stimulation circuit able to produce stimulation pulses in monopolar mode and/or a bipolar mode, a connector head coupled to the metallic case that is equipped with at least two terminals that are able to be connected to electrodes of a probe for detection and stimulation, such that the terminals can be coupled to a monopolar probe or a bipolar probe. The generator includes means for detecting the presence of a probe connected to the connector head.

In a manner characteristic of the invention, the probe detecting means includes: means for producing monopolar or bipolar stimulation pulses, selectively and with or without a disconnection of a connection between the terminal(s) to a reference potential (hereinafter a "reference potential connection"); means for detecting at least one pulse signal produced by the variation of potential induced on one and/or the other of the terminals and/or on the metallic case by the application of the aforesaid stimulation pulses; discriminating means, able to analyze a characteristic of the shape of said at least one detected pulse signal and to deliver an indicator representative of the presence or absence of a probe; and control means, to selectively modify at least one operating parameter of the device according to the indicator delivered by the discriminating means. Preferably the shape characteristic is the width of the at least one detected pulse signal, and the width is compared to a predetermined threshold.

According to a first embodiment of the invention, the means for producing stimulation pulses operates to apply a stimulation pulse with a disconnection of the reference potential connection, and the discriminating means operates to compare the width of the pulse signal detected on the terminal of the proximal electrode and on the case to a given threshold. The discriminating means can then deliver an indicator, i.e., a parameter representative of:
1. the absence of a probe or a non-implantation of the case after connection of a probe when the width of the detected pulse signal on the case is below the threshold;
2. the presence of a monopolar probe implanted when the width of the detected pulse signal on the case is greater than or equal to the threshold and the width of the detected pulse signal on the terminal of the proximal electrode is below the threshold; or
3. the presence of an implanted bipolar probe when the width of the detected pulse signal on the case and on the proximal terminal is greater than or equal to the threshold.

If, in another case, the means for producing stimulation pulses apply a bipolar stimulation pulse without a disconnection of the reference potential connection, the discriminating means can, by comparing the width of the detected pulse signal on the case with a low threshold and a high threshold, deliver an indicator representative of:
1. the presence of a bipolar probe when the width of the detected pulse signal on the case is below the low threshold;
2. the absence of a probe when the width of the detected pulse signal on the case is included between the low threshold and the high threshold; or
3. the presence of a monopolar probe when the width of the detected pulse signal on the case is approximately equal to the high threshold.

If, in the following case, the means for producing stimulation pulses apply a monopolar stimulation pulse without disconnection of the reference potential, the discriminating means can deliver a representative indicator of:
1. The absence of a probe when the width of the detected pulse signal on the case is included between the low threshold and the high threshold;
2. The presence of a bipolar probe when the width of the detected pulse signal on the terminal of the proximal electrode is below the low threshold; or
3. The presence of a monopolar probe when the width of the detected pulse signal on the terminal of the proximal electrode is equal or approximately equal to the high threshold.

According to an alternative embodiment of the invention, the means for producing stimulation pulses apply a bipolar stimulation pulse between the terminal of the proximal electrode and terminal of the distal electrode, without disconnection of the reference potential connection, and the discriminating means compares the width of the detected pulse signal on the case with a high threshold and a low threshold. The discriminating means can then deliver a representative indicator of:
1. The absence of a probe or the non-implantation of the case after connection of a probe when the width of the detected pulse signal on the case is included between the two thresholds;
2. The presence of a bipolar probe when the width of the detected pulse signal on the case is below the low threshold; or
3. The presence of a monopolar probe when the width of the detected pulse signal on the case is equal to or approximately equal to the high threshold.

Advantageously, the control means, starting from an initial state of the device in which, before implantation, it operates temporarily in a sleep mode with reduced functionalities, on the delivery of an indicator representative of the presence of a probe, switches the device to a fully functional mode. The control means, on delivery of an indicator representative of the presence of a probe, also can carry out at least one action selected from among: activation of the analog detection circuits; activation of any physiological or activity sensor that may be present in, for example, a rate responsive cardiac pacing system; programming of the type of stimulation, monopolar or bipolar, according to the delivered indicator; initialization of the control algorithms for operation of the device; resetting and activation of the counter of diagnosis; and inscription in the memory of the date of implantation.

It can also be envisaged to provide optionally a safety mechanism whereby, when the device operates in bipolar stimulation on a bipolar probe and in the event of delivery of an indicator that is not representative of the presence of a bipolar probe, it switches the device to a safety mode of operation with monopolar stimulation. In the same way, when the device receives from an external programmer an instruction parameter for setting the stimulation mode to bipolar, then the safety means authorizes the activation of the bipolar stimulation mode only if the discriminating means delivers an indicator representative of the presence of a bipolar probe.

BRIEF DESCRIPTION OF THE DRAWINGS

Further benefits, features and characteristics of the present invention will become apparent to a person of ordinary skill in the art in view of the following detailed description of preferred embodiments of the invention, made with in reference to the annexed drawings, in which:

FIG. 1 is a diagrammatic representation of the device according to the invention, with a generator equipped with a bipolar probe;

FIGS. 2 to 5 represent, for four different situations, on the one hand (on the left) the equivalent electric circuit seen from the terminals of the device and on the other hand (on the right) the shapes of the pulses likely to be detected on the various terminals of the device at the application of a stimulation pulse in the case where the reference potential connection is voluntarily disconnected;

FIGS. 6 to 8 are homologous with FIGS. 2 to 5, in the case where a reference potential connection is established;

FIG. 9 is a flow chart showing the various steps of an embodiment of an algorithm for detecting the presence of a probe and the type of probe, as well as actions taken consequently;

FIG. 10 is a flow chart showing an embodiment of a way in which it is possible to detect a loss of integrity of a bipolar probe.

DETAILED DESCRIPTION OF THE INVENTION

Figure 11:
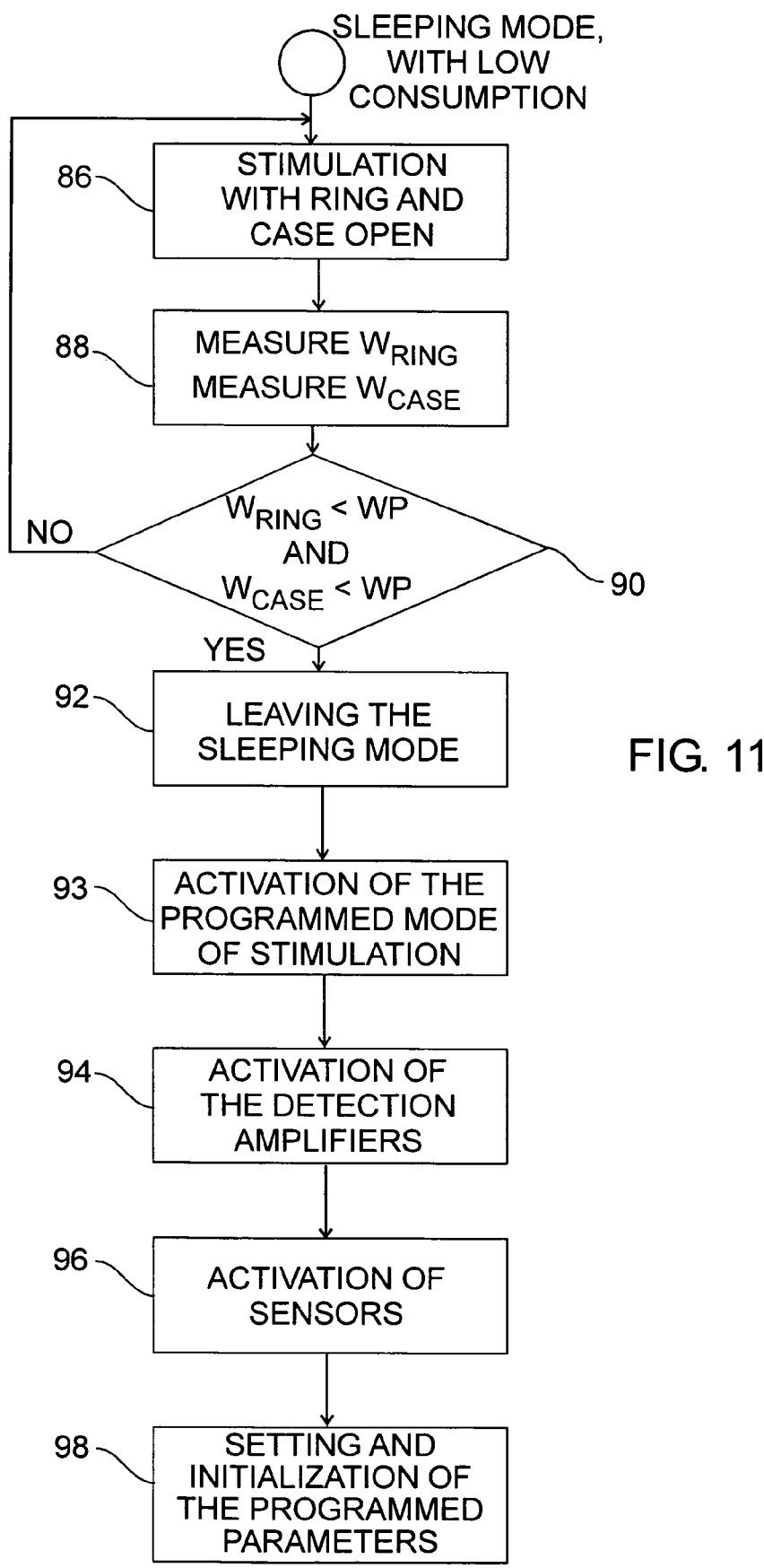
FIG. 11 is a flow chart showing the various steps of an embodiment of an algorithm making it possible, on the one hand, to increase the lifespan of the device by deactivation before the implantation (i.e., entering a sleep mode) and, on the other hand, the detection of the configuration where the case, after having been equipped with a bipolar probe, was not yet introduced by the surgeon into the pocket.

FIG. 1 represents, in a diagrammatic way, a cardiac pacemaker (or a device including the functions of cardiac detection and stimulation), primarily including a generator 10 and a stimulation probe 12. Probe 12 is illustrated as a bipolar probe, thus including two electrodes: a distal electrode 14, at the end of probe 12, connected to terminal 16 of the generator, terminal 16 generally indicated "TIP"; and a proximal electrode 18, typically of an annular shape, connected to another terminal 20 of generator, generally indicated "RING". The shapes of the proximal and distal electrodes should be understood to be non limiting.

In addition, the metallic case of the generator 10 is connected internally on a terminal 22, generally indicated "CASE". Terminal 22 is used as reference potential compared to electrodes RING and TIP for the collection of the depolarization potentials and/or the application of stimulation pulses.

Generator 10 comprises a voltage source circuit (buttery) 24 ensuring the charge of a capacitor of large capacity $C_{STO}$. Capacitor $C_{STO}$, once charged, makes it possible to deliver the stimulation pulse on closing of switch 26. Switch 26 is controlled by a control signal STIM delivered by the microcontroller (not shown) in a conventional manner. The closing of switch 26 causes a transfer of the energy accumulated in capacitor $C_{STO}$ towards terminal TIP 16, via a decoupling capacitor $C_{OUT}$.

In the case of a bipolar probe (as illustrated on FIG. 1), terminal RING 20 typically constitutes the electric reference, and thus is connected to the internal ground of the generator by closing of a switch $S_1$ controlled by a signal BIP produced by the microcontroller. When switch $S_1$ is open, a resistance $R_1$ is inserted between the ground G and electrode 20. In addition, a capacitor $C_1$ between terminals 16 and 20 ensures a protection against the various electromagnetic interferences.

In a monopolar mode, terminal CASE 22 typically constitutes the electric reference, and is connected to the internal ground of the generator by closing of a switch $S_2$ controlled by a signal MONOP produced by the microcontroller. When switch $S_2$ is open, a resistance R2 is inserted between the ground G and the electrode 22. In addition, a capacitor $C_2$ between the terminals 16 and 22 ensures a protection against the various electromagnetic interferences.

Essentially, the mechanism of detecting a probe, and the type of probe, according to a preferred embodiment of the present invention, concerns applying bipolar or monopolar stimulation pulses, with or without a disconnection of the reference potential connection, and observing the signals produced on electrodes CASE and RING. These signals will be notably different according to whether the generator:

1. is not implanted and is not equipped with a probe,
2. is equipped with a bipolar probe but not yet implanted,
3. is implanted and equipped with a bipolar probe, or
4. is implanted and equipped with a monopolar probe.

As one will describe herein, this discrimination can be carried out by an analysis of the detected pulse width and a comparison of that width with various thresholds.

A first possibility, illustrated in FIGS. 2 to 5, concerns delivering a stimulation pulse with the two reference potential connections disconnected (i.e., switches $S_1$ and $S_2$ open), and observing the waveforms collected on electrodes RING and CASE. This possibility, although it requires the analysis of the signal on two electrodes and the delivery of a stimulation pulse that does not capture the heart (i.e., does not cause a depolarization of the myocardium), presents the advantage of authorizing the detection of a partially implanted device, with a bipolar probe connected to the generator but the case located out of the pocket. This faculty can be used in particular, as described below, "to awaken" the generator by making it leave the "sleep" mode at low energy consumption, and, by carrying out a certain number of initialization steps, as described below with reference in particular to the flow chart of FIG. 11.

Another possibility, illustrated by FIGS. 6 to 8, concerns delivering a stimulation pulse with the two reference potential connections intact (i.e., switches $S_1$ and $S_2$ closed). In the following description, one will consider in this case that the applied stimulation pulse is a bipolar pulse, i.e., one applied between terminals TIP and RING. But the invention could be implemented in a comparable manner by applying a monopolar stimulation pulse (thus between electrodes CASE and TIP) and by observing the shape of the detected pulse on electrode RING. This latter alternative, although less advantageous, should nevertheless be understood as within the framework of the present invention.

The detection of the presence of a probe, and of the type of probe, and of an effective implantation, is operated by a pulse width detecting circuit 28 that determines the width of the pulses collected on terminals CASE 22 and RING 20.

One now will describe, in reference to FIGS. 2 to 5, a preferred embodiment of the invention making it possible to detect the connection of a probe and the generator implantation. In the initial state, at the time of shipping of the device, no probe is connected. The external configuration 30 (FIG. 2) of electrodes CASE, RING and TIP as seen by the device thus corresponds to a very high impedance, theoretically infinite (an open circuit), between two of these three terminals. Under these conditions, a stimulation pulse applied by the device with the two reference potential connections disconnected (i.e., switches S1 and S2 open) has the shape illustrated in FIG. 2, namely a shape of rectangular crenel (squarewave) with height $V_{STIM}$ and width $W_P$. In this configuration, terminals CASE and RING are coupled on terminal TIP by means of the respective protective capacitors $C_2$ and $C_1$. Detector circuit 28 thus will see on these terminals CASE and RING pulses such as illustrated on FIG. 2, with a abrupt step increment then a decaying return to the initial level according to a time-constant defined by $R_1$ and $C_1$ or $R_2$ and $C_2$. The duration $W_o$ at the middle height of the detected pulse is in this example about 200 µs.

FIG. 3 illustrates the case where the pacemaker is equipped with a bipolar probe, but where the case of the generator is neither implanted in the pocket nor connected to a reference potential electrode or a plate. It is about a particular configuration that must be detected to prevent a monopolar stimulation on a bipolar probe. In this case, the network of impedances 30, seen internally by the pacemaker, comprises only one impedance $RL_2$ between the two electrodes RING and TIP, because electrode CASE is electrically in the air (floating). The stimulation pulse applied to terminal TIP always has the shape of a crenel and the detected pulse on terminal CASE takes the same shape as that previously described in FIG. 2, because of the only-internal coupling by the protective capacitor $C_2$, with an abrupt step increase followed a progressive return to the initial level. On the other hand, the pulse collected on terminal RING presents the shape of a crenel similar to the stimulation pulse delivered on terminal TIP, because of the external coupling by impedance $RL_2$.

FIG. 4 illustrates the case where the pacemaker is equipped with a bipolar probe, with the case of the generator implanted in the pocket or connected to a reference electrode. In this case, the network of impedances 30 corresponding to this probe, seen internally by the pacemaker, includes impedances $RL_1$, $RL_2$ and $RL_3$ between three electrodes TIP, CASE and RING taken two by two. The pulses collected on terminals CASE and RING present then both the shape of a crenel similar to the stimulation pulse delivered on terminal TIP, because of the external coupling with terminal TIP by impedances $RL_1$, $RL_2$ and $RL_3$.

The case illustrated in FIG. 5 is the one where the pacemaker is equipped with a monopolar probe, with the case of the generator implanted in the pocket or connected to a reference electrode. One will note that with a monopolar probe, if the case is neither implanted nor connected to a reference electrode, the situation is identical to that depicted in FIG. 2. The pacemaker being by default in a monopolar stimulation mode (as a normal factory adjustment), this situation does not present a risk and no particular safety measure needs to be taken before the complete functional activation of the device. The configuration of impedance 30 is that illustrated in FIG. 5, namely a single impedance $RL_1$ between CASE and TIP, and with a very high impedance, theoretically infinite, between on the one hand RING and CASE, and on the other hand RING and TIP. The detected pulse on terminal CASE presents the shape of a crenel similar to the stimulation pulse delivered on terminal TIP, because of the external coupling by impedance $RL_1$. On the other hand, the pulse collected on terminal RING presents an abrupt step followed by a progressive return to the initial level, because of the internal coupling by the protective capacitor $C_1$.

Thus, a simple analysis of the detected pulses on terminals CASE 22 and RING 20 by the detecting circuit 28 make it possible to discriminate between a generator that is not implanted (FIG. 2) and a partially implanted generator (FIGS. 3 to 5). In the case of a generator that is not implanted, the width of the signal that is also detected on terminals CASE or RING is $W_O$. As soon as a probe is connected, the detected pulse width on terminals CASE and/or RING becomes $W_P$. This discrimination makes it possible to detect immediately, i.e., in the interval of a cardiac beat, the connection, even partial, of a bipolar or monopolar probe, and whether the generator is or is not placed in the pocket. This detection is in particular used "to awaken" the generator immediately. This is so that the generator leaves a low energy consumption mode and commutates to a mode where it will be fully functional, with, in particular preference, a safety stimulation ensuring the capture by the stimulation pulse throughout the implantation procedure. The implementation of these functions will be described more in detail below with reference to the flow chart of FIG. 11.

One now will describe, with reference to FIGS. 6 to 8, the way in which the invention makes it possible to detect whether the device was correctly implanted and the implantation phase is completed. With this intention, one applies a bipolar pulse (for example) with the two reference potential connections established (i.e., switches $S_1$ and $S_2$ closed) and one analyzes the shape of the detected signal on terminals TIP and CASE.

FIG. 6 shows the shape of the pulse collected on terminal CASE for a bipolar pulse applied between terminals TIP and RING, when the generator is not implanted. The pulse observed on terminal CASE presents a step increment followed by a relatively slow exponential decay, defined by the time-constant of the internal components $R_1$ and $C_1$, the $W_o$ duration of the pulse at one-half the maximum excursion ("half height") being approximately 200 µs.

FIG. 7 shows the shape of the pulse collected on terminal CASE when the bipolar pulse is applied with the generator correctly implanted and equipped with a bipolar probe. In this case, the circuit of the generator sees three impedances $RL_1$, $RL_2$ and $RL_3$ between three respective terminals TIP, CASE and RING for the probe. The shape of the pulse observed on terminal CASE when a stimulation pulse is applied between terminals TIP and RING falls with $V_{STIM}$ and goes up quickly, with a time-constant $RL_1/(RL_2+RL_3)$

*$C_1$. For a maximum impedance of 2 kilohms, the maximum duration of the pulse is less than 20 µs, a value defining a low threshold $W_{MIN}$.

FIG. 8 shows the shape of the pulse collected on terminal CASE when the bipolar pulse is applied between terminals TIP and CASE with the generator correctly implanted and equipped with a monopolar probe. In this case, the impedance between TIP and CASE are only that of tissues, while the impedance between TIP and RING, or between RING and CASE, is very high, theoretically infinite. The shape of the signal observed on terminal CASE is this practically the same one as that of the pulse detected on terminal TIP, because of low impedance $RL_1$ coupling terminals CASE and TIP.

Thus, the simple analysis by the detecting circuit 28 of the width of the pulse on terminals CASE 22 and RING 20 (width taken, for example, at half-height) makes it possible to determine the configuration of impedances and thus the three cases just described. This in turn allows the device to determine the presence of a probe, the type of probe and the integrity of the return circuit to ground resulting from an effective implantation in the pocket. Circuit 28 is a circuit in which the thresholds of detection are programmed, i.e., under microprocessor control, in a suitable manner way to discriminate in a non ambiguous way the three cases of possible waveforms as just described. For example, a high threshold is 500 µs, a low threshold is 100 µs.

One now will describe the operation of an embodiment the device of the invention, with reference to the flow charts of FIGS. 9 to 11. In the description relating to the flow charts of FIGS. 9 and 10, for the clearness of discussion one will disregard the specific protection corresponding to the particular case where the pacemaker was equipped with a bipolar probe, but where the case of the generator is neither implanted in the pocket, nor connected to a reference potential electrode or plate, as this particular situation will be treated with reference to the flow chart of FIG. 11.

FIG. 9 is a flow chart showing the various steps of the algorithm making it possible to detect the implantation of the device and to parameterize it consequently. After installation of the battery (not shown in FIG. 9, but see voltage source 24, FIG. 1), at the time of shipping (t=0) and after initialization of a counter N (step 32), the generator operates in a stimulation mode known as a "safety mode" with simultaneous delivery of bipolar and monopolar stimulation pulses (step 34), at a relatively low frequency, about 70 bpm. In this way, when a probe is connected to the generator terminals by the surgeon immediately before the implantation itself, the pulses will be already delivered on the electrode (or the electrodes) of the probe, whether the latter is monopolar or bipolar. After a predetermined period of time T (step 36), the generator detects the width W of the pulse on terminal CASE ($W_{CASE}$) of the generator operating in a bipolar stimulation mode (step 38). If the width W is greater than a predetermined threshold value $W_{MIN}$ and less than the pulse width $W_P$ of the stimulation pulse (step 40), then the device is not yet implanted, and it remains in the safety stimulation mode returning to step 34.

In the contrary case (step 42), counter N is decremented by one and, if it is not null (zero) (step 44), the counting of the period T is re-initialized (step 46) and the device returns at step 34 to the safety stimulation mode. The opposite case means that the test of step 40 detected three times consecutively on terminal CASE a pulse having a width W that is lower than $W_{MIN}$ or equal to $W_P$, i.e., it detected the presence of a probe. Therefore, it determines that the device was definitively implanted. By precaution, the period T is preferably selected so that 3×T corresponds to a duration greater than the average duration of an implantation, i.e., 3×T>20 minutes approximately.

Once the presence of a probe is detected, the pacemaker determines, according to the pulse width $W_{CASE}$ on terminal CASE, whether it is a bipolar or a monopolar probe (steps 48, 50 and 52). If the pulse width $W_{CASE}$ is less than $W_{MIN}$, the implanted probe is a bipolar probe, whereas otherwise it is a monopolar probe. The safety stimulation mode is then stopped (step 54) and stimulation in the determined programmed mode is activated (step 56).

After step 56, a verification algorithm is also activated, according to the invention, providing a continual checking of the integrity of the probe (step 58) (described more in detail with reference to FIG. 10). Lastly, the appropriate physiological algorithms are initialized (step 60), the counters of diagnosis are reset to zero and activated (step 62) and, if the device is equipped with a real time clock, the date of implantation is registered in memory (step 64).

FIG. 10 illustrates the way in which the process of the invention, in accordance with a preferred embodiment, allows the uninterrupted monitoring of the integrity of a bipolar probe after implantation. This process in particular makes it possible to detect a rupture of the wire of the proximal electrode 18, that would have as a consequence a loss of capture likely to involve significant risks for the patient. This rupture causes a modification of the impedance of the equivalent circuit 30 so that the pulse received on terminal CASE will present the illustrated shape, with a width $W_P$. Consequently, if bipolar stimulation is programmed (step 66), and if the pulse width $W_{CASE}$ collected on terminal CASE is less than threshold $W_{MIN}$ (step 68), this means that the probe is functional (see below). Bipolar stimulation is then continued (return at step 66, and counter N is set to a predetermined value, for example, N=3).

In the contrary case, the bipolar probe behaves like a monopolar probe, which is revealed by a shortening of the pulse collected on terminal CASE to a width appreciably equal to $W_P$ (i.e., not significantly less that $W_p$. On this event, which presumes that $W_p$ was previously less than $W_{MIN}$, the device switches to a monopolar stimulation mode (step 72) for safety. This condition is temporary, until its confirmed by three successive concordant tests during a given interval of time T (steps 72 to 82). If the defect is thus confirmed, then the pacemaker switches definitively to monopolar stimulation (step 84).

It will be noted that this process can be also used to prevent a physician mistakenly reprogramming a bipolar stimulation on a device that had been implanted with a monopolar probe, a situation which would have the same consequences as the rupture of the wire of proximal electrode of a bipolar probe.

Thus, after the physician has programmed a bipolar stimulation mode, the device produces the first bipolar stimulation and detects on terminal CASE a pulse of a certain width $W_{CASE}$. If this width $W_{CASE}$ is less than $W_{MIN}$, the configuration is in conformity and the modification of programming is accepted. In the contrary case, then the implanted probe is a monopolar probe, incompatible with a bipolar stimulation, and the change of programming mode is refused by the device.

Referring now to FIG. 11, it illustrates the way in which the process of the invention, in a preferred embodiment, can be used to improve the lifespan of the device, and to take into account the particular case where the pacemaker was equipped with a bipolar probe, but where the case of the generator is neither implanted in the pocket, nor connected to a reference potential electrode or plate.

It is known that many functions of the device involve a high current consumption, but are not necessary prior to an implantation. The lifespan of the battery, and thus the expiration date (i.e., the "use before" date) of the device before implantation, can be improved if these functions are deactivated at the shipping of the device, and automatically activated when the connection to a probe is detected. As illustrated on FIG. 11, with the delivery, the generator is in a sleep mode, consuming a low current. In particular, the analog circuits (detection amplifiers, circuits of polarization of the sensors and analog circuits for the treatment of the signals) are de-activated and the functions of the microcontroller are reduced to the minimum, with a simple stimulation at slow intervals, for example, 70 bpm on the atrium and the ventricle, a stimulation rate sufficient for the detection of a probe (steps 86 to 90).

As soon as the presence of a probe, atrial or ventricular, is detected, and the effective implantation is confirmed or the case is connected to a reference electrode (step 90), where one then tests whether the width $W_{CASE}$ of the pulse on terminal CASE is appreciably equal to (i.e., not significantly less than width $W_P$ of the pulse of stimulation), the device switches operating mode, leaving the sleep state mode having an initial set of operating parameters involving low energy consumption (step 92), by activating the programmed stimulation mode, monopolar or bipolar (step 93), by starting the activation of the detection amplifiers and other analog circuits (step 94), by activating any physiological or activity sensors present (step 96), and by restoring a general set of programmed operating parameters with full activation for the programmed mode (step 98).

Suitable devices for which the present invention has application include, for example, the NewAge™ pacemaker from Sorin CRM (Saluggia, Italy). These devices are microprocessor based systems with memory, data registers and the like (microcontrollers) having circuits for receiving, conditioning and processing detected electrical signals, providing stimulation pulses and detecting myocardial activity including the pulse width detection. Of course any such circuits as are available and known to those skilled in the art, including the aforementioned switches may be used as well as circuits able to perform these functions not yet commercialized. The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. An active implantable medical device, in particular a cardiac pacemaker, defibrillator, cardiovertor and/or "multisite" device, for use with a detection and stimulation probe allowing the delivery to the heart of the pulses of low energy for the treatment of the disorders of the cardiac rhythm, comprising, a metallic case containing a generator and a connector head, said generator being selectively configured to produce stimulation pulses in a monopolar mode and in a bipolar mode, said connector head comprising at least a first terminal and a second terminal able to be connected to a stimulation probe;

said generator further comprising a reference potential, a first switch controllable to connect and disconnect said first terminal to said reference potential, and a second switch controllable to connect said second terminal to said reference potential, and means for detecting the presence of a probe connected to the connector head, said probe being able to be a monopolar probe or a bipolar probe;

wherein said probe detecting means further comprises:

means for selectively producing monopolar stimulation pulses to one of said first and second terminals and bipolar stimulation pulses to said first and second terminals and controlling said first and second switches, wherein said stimulation pulses are deliverable, selectively with or without a reference potential connection;

means for detecting at least one pulse signal corresponding to a variation of potential induced on one of said first and second terminals and the metallic case in response to an applied stimulation pulse;

discriminating means for analyzing the pulse width of said at least one detected pulse signal and for delivering an indicator as a function of said analyzed pulse width representative of the presence or absence of a probe connected to said connector head; and control means for selectively modifying at least one operating parameter according to the delivered indicator.

2. The device of claim 1, wherein said first terminal further comprises a ring terminal for coupling to a proximal ring electrode of a bipolar probe and the means for selectively producing stimulation pulses further comprises means for applying a stimulation pulse and controlling said first and second switches to obtain a disconnection of the reference potential connection, wherein said discriminating means further comprises means for comparing to a first threshold the pulse signal width detected on the ring terminal and the metallic case.

3. The device of claim 2, wherein discriminating means further comprises means for determining that the width of the detected pulse signal on said metallic case is less than said first threshold, and means, in response thereto, for delivering an indicator representative of one of an absence of a probe and a non implantation of the metallic case after connection of a probe.

4. The device of claim 2, wherein discriminating means further comprises means for determining that the width of the pulse signal detected on the first terminal is less than said first threshold and the width of the pulse signal detected on the metallic case is greater than or equal to said first threshold, and means, in response thereto, for delivering an indicator representative of a presence of an implanted monopolar probe.

5. The device of claim 2, wherein the discriminating means further comprises means for determining that the width of the pulse signal detected on the metallic case and the first terminal is greater than or equal to said first threshold, and means, in response thereto, for delivering an indicator representative of the presence of an implanted bipolar probe.

6. The device of claim 1, wherein the means for selectively producing stimulation pulses further comprises means for applying a bipolar stimulation pulse and controlling said first and second switches to obtain a reference potential connection, wherein the discriminating means further comprises means for comparing the width of the pulse signal detected on the metallic case to a low threshold and to a high threshold.

7. The device of claim 6, wherein the discriminating means further comprises means for delivering an indicator representative of a presence of a connected bipolar probe in response to the width of the pulse signal detected on said case being less than said low threshold.

8. The device of claim 6, wherein the discriminating means further comprises means for delivering an indicator representative of an absence of a connected probe in response to said width of the pulse signal detected on said case being included between said low threshold and said high threshold.

9. The device of claim 6, wherein the discriminating means further comprises means for delivering an indicator representative of a presence of a connected monopolar probe in response to the width of the pulse signal detected on said case being not less than said high threshold.

10. The device of claim 1, wherein said first terminal further comprises a ring terminal for coupling to a proximal ring terminal of a bipolar probe and the means for selectively producing stimulation pulses further comprises means for applying a monopolar stimulation pulse and controlling said first and second switches to obtain a reference potential connection, and the discriminating means further comprises means for comparing the width of the pulse signal detected on the first terminal to a low threshold and a high threshold.

11. The device of claim 10, wherein the discriminating means further comprises means for delivering an indicator representative of an absence of a connected probe in response to the width of the pulse signal detected on said case being included between said low threshold and said high threshold.

12. The device of claim 10, wherein the discriminating means further comprises means for delivering an indicator representative of a presence of a connected bipolar probe in response to the width of the pulse signal detected on the first terminal being less than said low threshold.

13. The device of the claim 10, wherein the discriminating means further comprises means for delivering an indicator representative of a presence of a connected monopolar probe in response to the width of the pulse signal detected on the first terminal being not less than said high threshold.

14. The device of claim 1, wherein said first terminal corresponds to a proximal electrode of a bipolar probe and said second terminal corresponds to a tip electrode of a bipolar probe and the means for selectively producing stimulation impulses further comprises means for applying a bipolar stimulation pulse between the first and second terminals and controlling said first and second switches to obtain a reference potential connection, and the discriminating means further comprises means for comparing the width of the pulse signal detected on said metallic case to a high threshold and a low threshold.

15. The device of claim 14, wherein the discriminating means further comprises means for delivering an indicator representative of an absence of a connected probe or a non-implantation of the case in a presence a connected probe in response to the width of the pulse signal detected on said case being included between said high and low thresholds.

16. The device of claim 15, wherein the discriminating means further comprises means for delivering an indicator representative of a presence of a connected bipolar probe in response to the width of the pulse signal detected on said case being less than the low threshold.

17. The device of claim 15, wherein the discriminating means further comprises means for delivering an indicator representative of a presence of a connected monopolar probe in response to the width of the pulse signal detected on said case being not less than said high threshold.

18. The device of claim 1, wherein said generator comprises an initial set of operating parameters corresponding to a temporary operating mode with reduced functionalities and a general set of operating parameters corresponding to at least one fully functional operating mode, wherein the control means further comprises means for operating said generator in said initial set of operating parameters prior to a delivered indicator corresponding to an implantation and means for operating said generator in said general set of operating parameters in response to a delivered indicator representative of the presence of a connected probe.

19. The device of claim 18, wherein said control means, further comprises means, responsive to delivery of an indicator representative of the presence of a connected probe, for carrying out at least one of activating an analog circuit for detection of cardiac activity, activating a physiological or activity sensor; programming of a monopolar or bipolar type of stimulation according to the delivered indicator; initializing algorithms for the operation of the device; resetting and activating of a diagnosis counter; and the inscribing in a memory a date of implantation.

20. The device of claim 1, further comprising a safety means for switching operation of said devices to a mode of safety with monopolar stimulation, said safety means being responsive to the device operating in a bipolar stimulation for a connected bipolar probe and subsequent delivery of an indicator representative of an absence of a bipolar probe.

21. The device of claim 1, further comprises a safety means for authorizing a bipolar mode of stimulation only if the discriminating means delivers an indicator representative of the presence of a bipolar probe, said safety means being responsive to an instruction to set device operation to a bipolar mode of stimulation.

* * * * *